United States Patent [19]

McPherson

[11] 4,335,727
[45] Jun. 22, 1982

[54] PACEMAKER ASSEMBLY HAVING VENTRICULAR INHIBITED AND VENTRICULAR TRIGGERED PACEMAKER UNITS

[76] Inventor: William E. McPherson, P.O. Box 270882, Tampa, Fla. 33688

[21] Appl. No.: 154,880

[22] Filed: May 30, 1980

[51] Int. Cl.³ ............................................. A61N 1/36
[52] U.S. Cl. ............................................. 128/419 PG
[58] Field of Search ................................ 128/419 PG

[56] References Cited

U.S. PATENT DOCUMENTS

| | | | |
|---|---|---|---|
| 3,431,912 | 3/1969 | Keller, Jr. | 128/419 PG |
| 3,433,228 | 3/1969 | Keller, Jr. | 128/419 PG |
| 3,648,707 | 3/1972 | Greatbatch | 128/419 PG |
| 3,857,398 | 12/1974 | Rubin | 128/419 PG |

*Primary Examiner*—William E. Kamm
*Attorney, Agent, or Firm*—Finnegan, Henderson, Farabow, Garrett & Dunner

[57] ABSTRACT

A pacemaker assembly having a ventricular inhibited pacemaker unit set to produce a signal for application to a patient's heart at a first rate of time and a ventricular triggered pacemaker unit set to produce a signal for application to a patient's heart at a second rate of time lower than said first rate of time, both units being contained within a housing and being independently operative with respect to one another.

2 Claims, 2 Drawing Figures

PACEMAKER ASSEMBLY HAVING VENTRICULAR INHIBITED AND VENTRICULAR TRIGGERED PACEMAKER UNITS

BACKGROUND OF THE INVENTION

1. Field of the Invention

The invention relates to a pacemaker assembly having redundant ventricular inhibited and ventricular triggered pacemaker units.

2. Description of the Prior Art

The use of implanted cardiac pacemakers has received wide acceptance in the medical field in the treatment of patients having certain heart problems to prevent the patient's heart rate from falling below a predetermined number of beats per minute. Some patients are totally dependent on the pacemaker to cause their hearts to beat while others use their pacemakers only when their heart cannot maintain a heart rate that is sufficiently fast to supply an adequate amount of blood to the body.

Chemical body changes, drug levels, and disease can alter the heart's condition after a pacemaker has been implanted in a patient. It has been proven clinically that it is important that a pacemaker not compete with the patient's heart activity, i.e., not fire at random while the heart is adequately beating on its own. Thus a sick heart suffering from a lack of oxygen can be damaged by or caused to go into fibrillation if stimulated during the repolarization or T-wave cycle of the heart beat.

To prevent this, pacemakers having different modes of pacing are in use. Pacemakers, for example, may function in the ventricular inhibited or demand mode. This type of pacemaker is designed to operate at a preset or programmable number of beats per minute. For example, 70 beats per minute corresponds to a time interval between beats of 857 milliseconds. If a heartbeat is not detected within that period of time, the pacemaker fires causing a heartbeat. If a heartbeat is sensed during the preset time interval, the packemaker is automatically reset in response to the sensed heart activity and waits until the preset time interval again lapses before firing, if a heartbeat is not sensed, or resetting if a heartbeat is sensed.

Demand pacemakers have the advantage of conserving battery energy when it essentially remains dormant because of the patient's heart rate being faster than the rate at which the pacemaker is set to operate. However, this type of pacemaker has the disadvantage of its operation being subject to being inhibited by picking up signals other than a heartbeat, such as certain electromagnetic interference which causes it to reset even when a heartbeat is not produced by the patient.

Many sources of electromagnetic interference have been identified which can or will cause inhibition of demand pacemakers, which are generally designed to revert to asynchronous operation in the event of electromagnetic interference. In the asynchronous mode, stimulation is provided by the pacemaker at a predetermined rate without modification by spontaneous cardiac rhythm. Asynchronous operation is generally useful only for complete heart block without interpolated premature ventriculated contractions, and this is considered to be an unreliable design feature.

Another mode of pacing is the ventricular triggered mode, also known as R-wave synchronous or R-wave tracking pacemakers. Pacemakers functioning in this mode operate at a preset or programmable number of beats per minute. A stimulus is emitted into each QRS complex and distorts it. The sensing activity of this pacemaker differs from a ventricular inhibited or demand pacemaker in that it discharges a stimulus of energy into each sensed heartbeat that is faster than the pacemaker's preset rate. By stimulating the sensed R-wave it avoids stimulation of the T-wave. Because it does not revert to a dormant state when the heart is beating, it consumes more battery energy and reduces the life of the pacemaker's battery if the patient does have a faster heart rate than the pacemaker's programmed or set rate. However, one particular advantage of this type of pacemaker is that it is not inhibited by electromagnetic interference and consequently the heart will be paced even in the event electromagnetic interference is present.

The advantage of battery conservation in a demand pacemaker is not applicable to a patient totally dependent upon his pacemaker. The disadvantage of a shortened battery life in an R-wave synchronous pacemaker does not apply in the case of a patient totally dependent on his pacemaker.

The various modes of pacemaker operation and implantation techniques are described in medical publications. Attention is directed to the article entitled "Cardiac Pacing and Pacemakers v. Technical Aspects of Implantation and Equipment" by Furman et al, American Heart Journal, Vol. 94, No. 2, pp. 250–259 (August, 1977).

SUMMARY OF THE INVENTION

The instant invention provides a pacemaker assembly having particular advantages over prior art pacemakers. In accordance with the invention, a pacemaker assembly having a totally redundant system is used to avoid catastrophic failure.

The preferred embodiment of my invention comprises a pacemaker assembly including a combination of a ventricular triggered pacemaker unit operating in conjunction with a ventricular inhibited pacemaker unit, with the latter operating at a faster preset rate of time. The simultaneous operation of the pacemaker assembly in these two pacing modes is particularly useful in the case of patients where total pacemaker dependency is diagnosed or anticipated.

Each pacemaker unit preferably has preset or programmable rates, sensitivity, pulse width, and output voltage, and in the case of the ventricular inhibited unit, refractory period. The pacemaker assembly includes a single housing for the two pacemaker units. The combination of the two pacemaker units permits them to be checked with standard electrocardiogram (EKG) equipment to determine whether they are operating properly. Thus, if the ventricular inhibited pacemaker unit is functioning at a faster rate of time than the ventricular triggered unit, the EKG would pick up the emitted signal. If the ventricular inhibited unit is not operating, it will not produce a signal and the signal normally produced later in time by the ventricular triggered unit would be detected if that unit is operating properly. If a signal from the ventricular triggered unit is not detected by the EKG, this would indicate that the unit also is not functioning properly.

The two units operating independently of one another eliminate the chance of a patient dying due to an electronic malfunction in the pacemaker assembly. Failure of one unit will not affect the other unit and the chance of both units independently failing between checkups is highly remote. While external electromagnetic interference might cause the ventricular inhibited unit to shut down, the ventricular triggered unit will not be inhibited by such interference, thus eliminating another hazard.

DETAILED DESCRIPTION OF THE INVENTION

Figure 1:
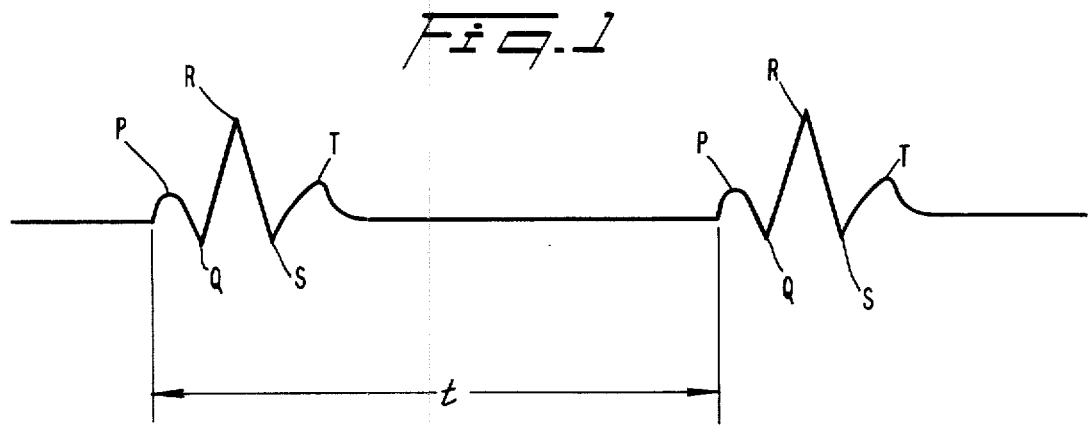
FIG. 1 is a plan view of the pacemaker assembly in accordance with the invention.
Figure 2:
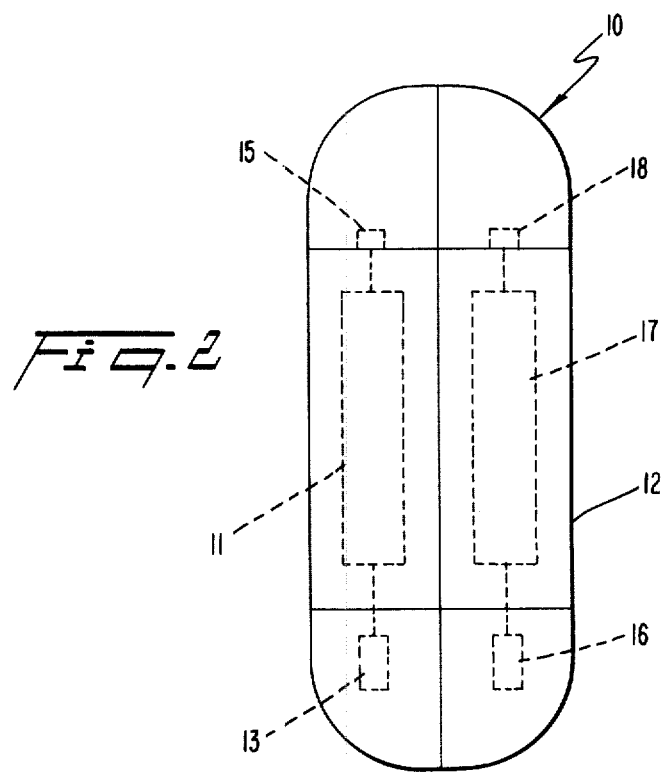
FIG. 2 is an EKG graph of the complex wave produced by a patient's heart.

FIG. 1 shows a pacemaker assembly 10 in accordance with the invention having ventricular inhibited pacemaker unit 11 and ventricular triggered pacemaker unit 12. Each pacemaker unit 11 and 12 is complete within itself in that each unit operates independently of the other. Ventricular inhibited or demand pacemaker unit 11 comprises battery 13, electronic circuitry 14 and connector 15. The battery 13 may typically comprise a lithium iodine battery to power the electronic circuitry 14 which produces the desired electrical signal stimulus at conductor 15 for application through appropriate leads (not shown) to the heart. Similarly, ventricular triggered or R-wave synchronous pacemaker unit 12 comprises its own battery 16 to power electronic circuitry 17 to produce the desired signal at connector 18 to provide an appropriate stimulus to the heart through connectors (not shown).

The independent pacemaker units 11 and 12 while operating completely independently are hermetically sealed with the housing 10. In the medical field, 72 beats per minute is generally accepted as a normal and standard heartbeat rate. The heart, however, will tolerate many rates faster and slower than 72 beats per minute. A ventricular inhibited or demand pacemaker unit does not function while the heart is beating at a faster rate than that to which the pacemaker is set. For example, a pacemaker set at 72 BPM will emit a pulse of energy every 832 milliseconds, unless the heart beats on its own prior to the expiration of that time interval. After a demand pacemaker senses the heartbeat, the pacemaker waits another 832 milliseconds before firing, if the heart does not beat first.

In accordance with the invention, the ventricular triggered pacemaker unit 12 is set to operate at a lower rate than the ventricular inhibited or demand pacemaker unit 11. For exemplary purposes only in describing the invention, if the ventricular inhibited pacemaker unit 11 is assumed to be set to produce a stimulus at the rate of 70 BPM, the ventricular triggered pacemaker unit 12 may be assumed to be reset to operate at the rate of 60 BPM. Thus pacemaker unit 11 would emit a stimulus every 857 milliseconds and unit 12 would produce a stimulus every 1,000 milliseconds.

Assume, for the purpose of explaining the invention, that a patient's heart is operating at 72 beats per minute, demand pacemaker unit 11 is set to operate at 70 BPM, and ventricular triggered pacemaker unit 12 is set to function at 60 BPM. Under these conditions, the patient's normal heartbeat is faster than the setting of either pacemaker units 11 and 12 and demand pacemaker unit 11 will sense the heartbeat before it can emit a stimulus and consequently will be inhibited from emitting it. The ventricular triggered unit 12 is set to operate when it senses a signal from the heart. However, pacemaker unit 12 cannot identify whether the signal it senses results from the patient's heart or from operation of the demand pacemaker unit 11. In the instance where the patient's heart is operating at 72 BPM, unit 12 will sense the heartbeat and will emit a stimulus into each QRS complex and distort the manual QRS complex. If the patient's heartbeat slows to a rate which is lower than the rate at which pacemaker unit 11 is set to operate, ventricular triggered pacemaker unit 12 will detect the signal applied to the heart by pacemaker unit 11 and will emit its own stimulus at that time. Thus, in the example given, ventricular triggered unit 12 operates at least once every 1,000 milliseconds, or at a faster rate depending upon the relative setting of demand unit 11 and the patient's actual heartbeat rate.

FIG. 1 shows an electrocardiogram produced by a patient's heartbeat. The respective sections labeled P, Q, R, S, and T are accepted designations to identify particular portions of the complex of waves produced by the heart. The ventricular triggered or R-wave synchronous pacemaker unit 12 is designed to track the R-wave portion of the complex of waves and emits a signal only into the R-wave portion between points Q and S. By so doing, it avoids applying a signal into the T-wave portion and the problems associated with producing an additional stimulus at that time which, as explained above, could be detrimental to the patient.

The pacemaker assembly in accordance with the instant invention provides distinct advantages over the prior art. Thus failure of one unit will not affect operation of the other unit and the chance of both units independently failing between checkups is very slight. Further, shut-down of demand pacemaker unit 11 due to the electromagnetic interference will not inhibit operation of the ventricular triggered unit 12, thereby eliminating another hazard.

There are many possible causes of pacemaker breakdowns. Battery failure, component failure, loss of hermeticity, contamination, mechanical malfunctions, electronic shorts or surges are some of the more prevalent types of breakdown. Such failures could result in sudden death to a patient who is totally dependent on the operation of his pacemaker. Further, knowledge of the possibility of such a failure and resulting sudden death can create a tremendous psychological problem for pacemaker patients which might have a deleterious effect on their health. The pacemaker assembly in accordance with applicant's invention solves this problem.

Applicant's pacemaker assembly is also advantageous because clinical verification of the operation of both pacemaker units 11 and 12 through the use of an EKG is possible. Thus, if a heartbeat is not sensed within the time period demand pacemaker unit 11 is set to operate, and that unit does not fire after that time, an electrocardiogram will reflect the breakdown of pacemaker unit 11. Further, if ventricular triggered unit 12 fires, either in response to a heartbeat or operation of pacemaker unit 11, the EKG will reflect that. If ventricular triggered unit 12 does not fire at all within the time period to which it is set to operate, the electrocardiogram will also indicate its breakdown.

Thus the pacemaker assembly in accordance with the invention provides clinically acceptable operation, efficient EKG verification of operability, and eliminates the risk of electromagnetic interference causing total inhibition of the pacemaker assembly. The simultaneous operation of a demand pacemaker unit and ventricular triggered unit in accordance with the pacemaker assembly of applicant's invention, where the ventricular triggered unit operates at a lower rate than the demand pacemaker unit is clinically possible, feasible, and practical where total pacemaker dependency is diagnosed or anticipated.

By the foregoing, there has been disclosed a preferred form of pacemaker assembly constructed in accordance with the present invention. It will be appreciated that various additions, substitutions, modifications and omissions may be made thereto without departing from the spirit of the invention.

I claim:

1. A pacemaker assembly comprising:
    a housing,
    a ventricular inhibited pacemaker unit set to produce a signal for application to a patient's heart at a first rate of time,
    a ventricular triggered pacemaker unit set to produce a signal for application to a patient's heart at a second rate of time lower than said first rate of time,
    the ventricular inhibited and ventricular triggered pacemaker units being contained within said housing and being independently operative with respect to one another.

2. The pacemaker assembly of claim 1 wherein said housing includes means for hermetically sealing the ventricular inhibited and ventricular triggered pacemaker units therein.

* * * * *